US012310987B2

(12) United States Patent
Hall et al.

(10) Patent No.: US 12,310,987 B2
(45) Date of Patent: May 27, 2025

(54) FIBROUS CONSTRUCTS WITH THERAPEUTIC MATERIAL PARTICLES

(71) Applicant: Merit Medical Systems, Inc., South Jordan, UT (US)

(72) Inventors: John Hall, Bountiful, UT (US); Wayne Mower, Bountiful, UT (US); John Hellgeth, Murray, UT (US); Rachel Oberg, North Salt Lake, UT (US); Doug Friedrichs, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 17/652,552

(22) Filed: Feb. 25, 2022

(65) Prior Publication Data

US 2022/0273708 A1  Sep. 1, 2022

Related U.S. Application Data

(60) Provisional application No. 63/154,288, filed on Feb. 26, 2021.

(51) Int. Cl.

| | | |
|---|---|---|
| *A61K 33/44* | (2006.01) | |
| *A61K 47/32* | (2006.01) | |
| *D01D 5/00* | (2006.01) | |
| *D01D 5/12* | (2006.01) | |
| *D01D 5/18* | (2006.01) | |
| *D01F 1/10* | (2006.01) | |
| *D04H 1/724* | (2012.01) | |
| *D04H 1/728* | (2012.01) | |

(52) U.S. Cl.
CPC .............. *A61K 33/44* (2013.01); *A61K 47/32* (2013.01); *D01D 5/0015* (2013.01); *D01D 5/12* (2013.01); *D01D 5/18* (2013.01); *D01F 1/10* (2013.01); *D04H 1/724* (2013.01); *D04H 1/728* (2013.01); *D10B 2509/00* (2013.01)

(58) Field of Classification Search
None
See application file for complete search history.

(56) References Cited

U.S. PATENT DOCUMENTS

| | | |
|---|---|---|
| 2,772,444 A | 12/1956 | Arthur et al. |
| 3,047,444 A | 7/1962 | Harwood |
| 3,203,365 A | 8/1965 | Bowe et al. |
| 4,043,331 A | 8/1977 | Martin et al. |
| 4,044,404 A | 8/1977 | Martin et al. |
| 4,096,227 A | 6/1978 | Gore |
| 4,127,706 A | 11/1978 | Martin et al. |
| 4,223,101 A | 9/1980 | Fine et al. |
| 4,323,525 A | 4/1982 | Bornat |
| 4,345,414 A | 8/1982 | Bornat et al. |
| 4,689,186 A | 8/1987 | Bornat |
| 5,167,890 A | 12/1992 | Sasshofer et al. |
| 5,344,297 A | 9/1994 | Hills |
| 5,552,100 A | 9/1996 | Shannon et al. |
| 5,562,986 A | 10/1996 | Yamamoto et al. |
| 5,620,763 A | 4/1997 | House et al. |
| 5,700,572 A | 12/1997 | Klatt et al. |
| 5,702,658 A | 12/1997 | Pellegrin et al. |
| 5,741,333 A | 4/1998 | Frid |
| 5,776,609 A | 7/1998 | McCullough |
| 5,810,870 A | 9/1998 | Myers et al. |
| 5,922,021 A | 7/1999 | Jang |
| 6,010,529 A | 1/2000 | Herweck et al. |
| 6,015,431 A | 1/2000 | Thornton et al. |
| 6,075,180 A | 6/2000 | Sharber et al. |
| 6,106,913 A | 8/2000 | Scardino |
| 6,156,064 A | 12/2000 | Chouinard |
| 6,165,212 A | 12/2000 | Dereume et al. |
| 6,306,424 B1 | 10/2001 | Vyakarnam |
| 6,383,214 B1 | 5/2002 | Banas et al. |
| 6,436,135 B1 | 8/2002 | Goldfarb |
| 6,498,207 B1 | 12/2002 | Hoshikawa et al. |
| 6,517,571 B1 | 2/2003 | Brauker et al. |
| 6,673,105 B1 | 1/2004 | Chen |
| 6,719,783 B2 | 4/2004 | Lentz et al. |
| 6,752,826 B2 | 6/2004 | Holloway et al. |
| 7,001,556 B1 | 2/2006 | Shambaugh |
| 7,115,220 B2 | 10/2006 | Dubson et al. |
| 7,118,698 B2 | 10/2006 | Armantrout et al. |
| 7,244,272 B2 | 7/2007 | Dubson et al. |

(Continued)

FOREIGN PATENT DOCUMENTS

| | | | |
|---|---|---|---|
| CN | 101584612 A | | 11/2009 |
| CN | 102560896 A | * | 7/2012 |

(Continued)

OTHER PUBLICATIONS

International Search Report and Written Opinion dated Jun. 14, 2022 for PCT/US2022/070844.
Cho , et al., "Self-Healing Polymer Coatings", Advanced Materials, 21, Jan. 1, 2009, 645-649.
Takmakov , et al., "Carbon Microelectrodes with a Renewable Surface", NIH Public Access, available in PMC, Anal Chem. 82(5), Mar. 1, 2010, 2020-2028.
European Examination Report dated Sep. 1, 2023 for EP20190128.7.
European Examination Report dated Jan. 2, 2024 for EP21165437.1.
European Examination Report dated Mar. 15, 2024 for EP21181412.4.
European Examination Report dated Oct. 20, 2023 for EP21189728.5.
Office Action dated Apr. 3, 2024 for U.S. Appl. No. 16/877,259.
EP Examination Report dated May 28, 2019 for EP12755426.9.

(Continued)

*Primary Examiner* — Melissa S Mercier
(74) *Attorney, Agent, or Firm* — Dorsey & Whitney LLP

(57) ABSTRACT

Sheets of material used in medical devices and filters are disclosed. The sheets may include a fibrous mat including a plurality of microfibers. The microfibers may include a polymer matrix and a plurality of additive particles. The additive particles may include carbon material particles, therapeutic micro particles, and any combination thereof. Medical devices and filters that use the sheets are disclosed. Methods of producing the sheets are also disclosed.

20 Claims, 8 Drawing Sheets

(56) References Cited

U.S. PATENT DOCUMENTS

| | | |
|---|---|---|
| 7,316,754 B2 | 1/2008 | Ide et al. |
| 7,416,559 B2 | 8/2008 | Shalaby |
| 7,485,141 B2 | 2/2009 | Majercak et al. |
| 7,498,079 B1 | 3/2009 | Donckers |
| 7,524,527 B2 | 4/2009 | Stenzel |
| 7,582,240 B2 | 9/2009 | Marin et al. |
| 7,655,175 B2 | 2/2010 | Michael et al. |
| 7,799,261 B2 | 9/2010 | Orr et al. |
| 7,857,608 B2 | 12/2010 | Fabbricante et al. |
| 7,914,568 B2 | 3/2011 | Cully et al. |
| 7,947,069 B2 | 5/2011 | Sanders |
| 7,981,353 B2 | 7/2011 | Mitchell et al. |
| 8,092,768 B2 | 1/2012 | Miller et al. |
| 8,178,030 B2 | 5/2012 | Anneaux et al. |
| 8,257,640 B2 | 9/2012 | Anneaux et al. |
| 8,262,979 B2 | 9/2012 | Anneaux et al. |
| 8,637,109 B2 | 1/2014 | Grewe et al. |
| 8,691,543 B2 | 4/2014 | Gaudette et al. |
| 8,771,582 B2 | 7/2014 | Phaneuf et al. |
| 9,034,031 B2 | 5/2015 | Anneaux |
| 9,198,999 B2 | 12/2015 | Hall |
| 9,655,710 B2 | 5/2017 | Eller |
| 9,856,588 B2 | 1/2018 | Anneaux |
| 10,010,395 B2 | 7/2018 | Puckett |
| 10,028,852 B2 | 7/2018 | Hall |
| 10,154,918 B2 | 12/2018 | Haselby et al. |
| 10,507,268 B2 | 12/2019 | Hall et al. |
| 10,675,850 B2 | 6/2020 | Hall et al. |
| 2001/0009979 A1 | 7/2001 | Weilandt et al. |
| 2001/0039446 A1 | 11/2001 | Edwin et al. |
| 2001/0049551 A1 | 12/2001 | Tseng et al. |
| 2001/0053929 A1 | 12/2001 | Vonesh et al. |
| 2002/0049489 A1 | 4/2002 | Herweck et al. |
| 2002/0077693 A1 | 6/2002 | Barclay |
| 2002/0082675 A1 | 6/2002 | Myers |
| 2002/0084178 A1 | 7/2002 | Dubson |
| 2002/0090725 A1 | 7/2002 | Simpson et al. |
| 2002/0107565 A1 | 8/2002 | Greenhalgh |
| 2002/0198588 A1 | 12/2002 | Armstrong et al. |
| 2003/0040772 A1 | 2/2003 | Hyodoh et al. |
| 2003/0050711 A1 | 3/2003 | Laurencin et al. |
| 2003/0060871 A1 | 3/2003 | Hill et al. |
| 2003/0074049 A1 | 4/2003 | Hoganson |
| 2003/0100944 A1 | 5/2003 | Laksin et al. |
| 2003/0114917 A1 | 6/2003 | Holloway et al. |
| 2003/0139797 A1 | 7/2003 | Johnson |
| 2003/0195611 A1 | 10/2003 | Greenhalgh et al. |
| 2003/0211135 A1 | 11/2003 | Greenhalgh et al. |
| 2004/0030377 A1 | 2/2004 | Dubson et al. |
| 2004/0033364 A1 | 2/2004 | Spiridigliozzi et al. |
| 2004/0038038 A1 | 2/2004 | Yeung |
| 2004/0051201 A1 | 3/2004 | Greenhalgh et al. |
| 2004/0054397 A1 | 3/2004 | Smith et al. |
| 2004/0167606 A1 | 8/2004 | Chouinard |
| 2004/0219345 A1 | 11/2004 | Armantrout et al. |
| 2005/0053782 A1 | 3/2005 | Sen et al. |
| 2005/0137675 A1 | 6/2005 | Dubson et al. |
| 2005/0171593 A1 | 8/2005 | Whirley et al. |
| 2005/0187605 A1 | 8/2005 | Greenhalgh et al. |
| 2005/0244453 A1 | 11/2005 | Stucke et al. |
| 2005/0244639 A1 | 11/2005 | Marin et al. |
| 2006/0142852 A1 | 6/2006 | Sowinski et al. |
| 2006/0200232 A1 | 9/2006 | Phaneuf et al. |
| 2006/0228435 A1 | 10/2006 | Andrady et al. |
| 2006/0233990 A1 | 10/2006 | Humphrey et al. |
| 2006/0259131 A1 | 11/2006 | Molaei et al. |
| 2007/0023131 A1 | 2/2007 | Farnsworth et al. |
| 2007/0031607 A1 | 2/2007 | Dubson et al. |
| 2007/0043428 A1 | 2/2007 | Jennings et al. |
| 2007/0087027 A1 | 4/2007 | Greenhalgh et al. |
| 2007/0207186 A1 | 9/2007 | Scanlon et al. |
| 2007/0244569 A1 | 10/2007 | Weber et al. |
| 2007/0269481 A1 | 11/2007 | Li et al. |
| 2007/0276477 A1 | 11/2007 | Lee et al. |
| 2008/0021545 A1 | 1/2008 | Reneker et al. |
| 2008/0029617 A1 | 2/2008 | Marshall et al. |
| 2008/0118541 A1 | 5/2008 | Pacetti |
| 2008/0119943 A1 | 5/2008 | Armstrong et al. |
| 2008/0188923 A1 | 8/2008 | Chu |
| 2008/0199506 A1 | 8/2008 | Horres et al. |
| 2008/0208323 A1 | 8/2008 | El-Kurdi et al. |
| 2008/0234812 A1 | 9/2008 | Pacetti |
| 2008/0242171 A1 | 10/2008 | Huang et al. |
| 2008/0281406 A1 | 11/2008 | Addonizio et al. |
| 2008/0286321 A1 | 11/2008 | Reneker et al. |
| 2008/0288044 A1 | 11/2008 | Osborne |
| 2008/0305143 A1 | 12/2008 | Chen et al. |
| 2008/0319535 A1 | 12/2008 | Craven et al. |
| 2009/0012607 A1 | 1/2009 | Kim et al. |
| 2009/0018643 A1 | 1/2009 | Hashi et al. |
| 2009/0030499 A1 | 1/2009 | Bebb et al. |
| 2009/0041978 A1 | 2/2009 | Sogard et al. |
| 2009/0082846 A1 | 3/2009 | Chobotov |
| 2009/0088828 A1 | 4/2009 | Shalev et al. |
| 2009/0127748 A1 | 5/2009 | Takahashi |
| 2009/0136651 A1 | 5/2009 | Larsen et al. |
| 2009/0160099 A1 | 6/2009 | Huang |
| 2009/0163994 A1 | 6/2009 | Quigley et al. |
| 2009/0227944 A1 | 9/2009 | Weber |
| 2009/0232920 A1 | 9/2009 | Lozano et al. |
| 2009/0248131 A1 | 10/2009 | Greenan |
| 2009/0248144 A1 | 10/2009 | Bahler et al. |
| 2009/0269429 A1 | 10/2009 | Lozano et al. |
| 2009/0280325 A1 | 11/2009 | Lozano et al. |
| 2009/0319034 A1 | 12/2009 | Sowinski |
| 2010/0013126 A1 | 1/2010 | Ishaque et al. |
| 2010/0063574 A1 | 3/2010 | Bogert |
| 2010/0076401 A1 | 3/2010 | Von Oepen et al. |
| 2010/0076543 A1 | 3/2010 | Melsheimer et al. |
| 2010/0093093 A1 | 4/2010 | Leong et al. |
| 2010/0129628 A1 | 5/2010 | Young |
| 2010/0193999 A1 | 8/2010 | Anneaux et al. |
| 2010/0233115 A1 | 9/2010 | Patel et al. |
| 2010/0280590 A1 | 11/2010 | Sun et al. |
| 2010/0304205 A1 | 12/2010 | Jo et al. |
| 2010/0323052 A1 | 12/2010 | Orr et al. |
| 2011/0030885 A1 | 2/2011 | Anneaux et al. |
| 2011/0087318 A1 | 4/2011 | Daugherty et al. |
| 2011/0089603 A1 | 4/2011 | Fabbricante et al. |
| 2011/0135806 A1 | 6/2011 | Grewe et al. |
| 2011/0142804 A1 | 6/2011 | Gaudette et al. |
| 2011/0156319 A1 | 6/2011 | Kurokawa et al. |
| 2011/0263456 A1 | 10/2011 | Harttig |
| 2012/0114722 A1 | 5/2012 | Ballard et al. |
| 2012/0201988 A1 | 8/2012 | Hansen et al. |
| 2012/0225602 A1 | 9/2012 | Qi et al. |
| 2012/0271396 A1 | 10/2012 | Zheng |
| 2012/0292810 A1 | 11/2012 | Peno et al. |
| 2012/0316633 A1 | 12/2012 | Flanagan et al. |
| 2013/0018220 A1 | 1/2013 | Vad |
| 2013/0023175 A1 | 1/2013 | Anneaux et al. |
| 2013/0053948 A1 | 2/2013 | Anneaux et al. |
| 2013/0059497 A1 | 3/2013 | Anneaux et al. |
| 2013/0079700 A1 | 3/2013 | Ballard et al. |
| 2013/0085565 A1 | 4/2013 | Eller et al. |
| 2013/0184808 A1 | 7/2013 | Hall et al. |
| 2013/0184810 A1 | 7/2013 | Hall et al. |
| 2013/0238086 A1 | 9/2013 | Ballard et al. |
| 2013/0268062 A1 | 10/2013 | Puckett et al. |
| 2013/0316103 A1 | 11/2013 | Anneaux et al. |
| 2013/0325109 A1 | 12/2013 | Anneaux et al. |
| 2014/0012304 A1 | 1/2014 | Lampropoulos et al. |
| 2014/0079758 A1 | 3/2014 | Hall et al. |
| 2014/0081386 A1 | 3/2014 | Haselby et al. |
| 2014/0081414 A1 | 3/2014 | Hall et al. |
| 2014/0086971 A1 | 3/2014 | Hall et al. |
| 2014/0265061 A1 | 9/2014 | Hall et al. |
| 2014/0273703 A1 | 9/2014 | Mower et al. |
| 2015/0081000 A1 | 3/2015 | Hossainy |
| 2015/0148459 A1* | 5/2015 | Pawloski ............ C08K 7/14 427/430.1 |
| 2015/0320542 A1 | 11/2015 | Gabriele et al. |
| 2015/0325209 A1 | 11/2015 | Ting et al. |
| 2016/0250048 A1 | 9/2016 | Hall et al. |

(56) References Cited

U.S. PATENT DOCUMENTS

| | | | |
|---|---|---|---|
| 2016/0331528 | A1 | 11/2016 | Parker |
| 2018/0064565 | A1 | 3/2018 | Mactaggart |
| 2019/0008665 | A1 | 1/2019 | Hall et al. |
| 2019/0060528 | A1 | 2/2019 | Skender et al. |
| 2019/0076276 | A1 | 3/2019 | Longo |
| 2019/0110911 | A1 | 4/2019 | Nae |
| 2020/0015987 | A1 | 1/2020 | Einav |
| 2020/0369016 | A1 | 11/2020 | Hall et al. |
| 2020/0369017 | A1 | 11/2020 | Hall et al. |
| 2020/0375725 | A1 | 12/2020 | Chobotov et al. |
| 2020/0383767 | A1 | 12/2020 | Eller et al. |
| 2021/0162098 | A1 | 6/2021 | Mower et al. |
| 2021/0290416 | A1 | 9/2021 | Hall et al. |
| 2022/0047783 | A1 | 2/2022 | Hall et al. |
| 2022/0048285 | A1 | 2/2022 | Hall et al. |
| 2022/0054252 | A1 | 2/2022 | Eller et al. |
| 2023/0157804 | A1 | 5/2023 | Eller et al. |
| 2023/0191005 | A1 | 6/2023 | Hall et al. |
| 2023/0311472 | A1 | 10/2023 | Hall et al. |
| 2024/0253343 | A1 | 8/2024 | Hall et al. |

FOREIGN PATENT DOCUMENTS

| | | | | |
|---|---|---|---|---|
| CN | 109157928 | A | 1/2019 | |
| EP | 2944711 | A1 * | 11/2015 | ............ A61K 33/26 |
| EP | 2944711 | B1 | 12/2017 | |
| GB | 1577221 | | 10/1980 | |
| JP | 2007531833 | | 11/2007 | |
| JP | 2013501539 | A | 1/2013 | |
| KR | 20100077913 | | 7/2010 | |
| KR | 20100108382 | | 10/2010 | |
| WO | 199800090 | | 1/1998 | |
| WO | 2003051233 | | 6/2003 | |
| WO | 2004090206 | | 10/2004 | |
| WO | 2005074547 | | 8/2005 | |
| WO | 2005098100 | | 10/2005 | |
| WO | 2006123340 | | 11/2006 | |
| WO | 2008097592 | | 8/2008 | |
| WO | 2009127170 | | 10/2009 | |
| WO | 2010083530 | | 7/2010 | |
| WO | 2010132636 | | 11/2010 | |
| WO | 2011017698 | | 2/2011 | |
| WO | 2012103501 | A1 | 8/2012 | |
| WO | 2012122485 | | 9/2012 | |
| WO | 2013109528 | | 7/2013 | |
| WO | 2013151778 | | 7/2013 | |
| WO | 2014007979 | | 1/2014 | |
| WO | 2014066297 | A1 | 5/2014 | |

OTHER PUBLICATIONS

International Search Report and Written Opinion dated Apr. 3, 2014 for PCT/US2013/076418.
International Search Report and Written Opinion dated Apr. 26, 2013 for PCT/US2013/021554.
International Search Report and Written Opinion dated Apr. 27, 2015 for PCT/US2015/011746.
International Search Report and Written Opinion dated Apr. 30, 2015 for PCT/US2015/012002.
International Search Report and Written Opinion dated May 1, 2014 for PCT/US2014/012043.
International Search Report and Written Opinion dated May 23, 2012 for PCT/US2012/023006.
International Search Report and Written Opinion dated Jun. 8, 2016 for PCT/US2016/019487.
International Search Report and Written Opinion dated Jun. 23, 2015 for PCT/US2013/076418.
International Search Report and Written Opinion dated Jun. 26, 2014 for PCT/US2014/024868.
International Search Report and Written Opinion dated Jul. 1, 2014 for PCT/US2014/023416.
International Search Report and Written Opinion dated Jul. 1, 2016 for PCT/US2016/020165.
International Search Report and Written Opinion dated Sep. 6, 2013 for PCT/US2013/046245.
International Search Report and Written Opinion dated Dec. 3, 2013 for PCT/US2013/060172.
International Search Report and Written Opinion dated Dec. 5, 2013 for PCT/US2013/060812.
Notice of Allowance dated Jan. 25, 2017 for U.S. Appl. No. 14/152,626.
Notice of Allowance dated Jan. 30, 2020 for U.S. Appl. No. 14/152,590.
Notice of Allowance dated Feb. 6, 2020 for U.S. Appl. No. 13/360,444.
Notice of Allowance dated Feb. 24, 2021 for U.S. Appl. No. 16/035,334.
Notice of Allowance dated Mar. 13, 2020 for U.S. Appl. No. 14/832,422.
Notice of Allowance dated Apr. 3, 2018 for U.S. Appl. No. 14/081,504.
Notice of Allowance dated Apr. 14, 2015 for U.S. Appl. No. 14/031,746.
Notice of Allowance dated May 9, 2018 for U.S. Appl. No. 15/053,232.
Notice of Allowance dated Jul. 11, 2016 for U.S. Appl. No. 13/826,618.
Notice of Allowance dated Aug. 7, 2020 for U.S. Appl. No. 14/207,344.
Notice of Allowance dated Sep. 3, 2015 for U.S. Appl. No. 13/787,327.
Office Action dated Jan. 13, 2015 for U.S. Appl. No. 13/827,790.
Office Action dated Jan. 14, 2019 for U.S. Appl. No. 13/827,790.
Office Action dated Jan. 16, 2018 for U.S. Appl. No. 14/081,715.
Office Action dated Jan. 17, 2019 for U.S. Appl. No. 14/832,422.
Office Action dated Jan. 22, 2016 for U.S. Appl. No. 14/152,626.
Office Action dated Jan. 23, 2017 for U.S. Appl. No. 14/081,715.
Office Action dated Jan. 25, 2019 for U.S. Appl. No. 14/207,344.
Office Action dated Feb. 4, 2015 for U.S. Appl. No. 13/360,444.
Office Action dated Feb. 7, 2017 for U.S. Appl. No. 13/827,790.
Office Action dated Feb. 8, 2019 for U.S. Appl. No. 14/081,715.
Office Action dated Feb. 16, 2018 for U.S. Appl. No. 13/742,077.
Office Action dated Feb. 20, 2015 for U.S. Appl. No. 14/044,050.
Office Action dated Feb. 20, 2020 for U.S. Appl. No. 15/806,020.
Office Action dated Feb. 22, 2016 for U.S. Appl. No. 13/742,077.
Office Action dated Feb. 26, 2015 for U.S. Appl. No. 14/152,590.
Office Action dated Mar. 3, 2014 for U.S. Appl. No. 13/742,025.
Office Action dated Mar. 15, 2017 for U.S. Appl. No. 14/207,344.
Office Action dated Mar. 25, 2020 for U.S. Appl. No. 14/081,715.
Office Action dated Mar. 28, 2016 for U.S. Appl. No. 13/827,790.
Office Action dated Mar. 31, 2017 for U.S. Appl. No. 14/204,466.
Office Action dated Apr. 6, 2020 for U.S. Appl. No. 13/827,790.
Office Action dated Apr. 7, 2017 for U.S. Appl. No. 13/826,618.
Office Action dated Apr. 27, 2017 for U.S. Appl. No. 13/742,077.
Office Action dated Apr. 29, 2020 for U.S. Appl. No. 14/207,344.
European Examination Report dated Jun. 4, 2024 for EP20199088.4.
Office Action dated Jun. 14, 2024 for U.S. Appl. No. 16/895,975.
Office Action dated Jun. 27, 2024 for U.S. Appl. No. 16/896,013.
Office Action dated Jul. 2, 2024 for U.S. Appl. No. 17/341,038.
Office Action dated Jul. 12, 2024 for U.S. Appl. No. 18/170,364.
Office Action dated Jul. 16, 2024 for U.S. Appl. No. 17/068,627.
Office Action dated Nov. 29, 2023 for U.S. Appl. No. 16/895,975.
Office Action dated Dec. 13, 2023 for U.S. Appl. No. 16/896,013.
Office Action dated Dec. 19, 2023 for U.S. Appl. No. 16/877,259.
Office Action dated Dec. 29, 2023 for U.S. Appl. No. 17/068,627.
European Search Report dated Oct. 11, 2024 for EP24173827.7.
Board Decision on Appeal dated Nov. 23, 2018 for U.S. Appl. No. 14/044,050.
Patent Board Decision—Reversed dated Dec. 6, 2022 for U.S. Appl. No. 13/742,077.
European Examination Report dated May 10, 2023 for EP20191283.9.
European Examination Report dated Jun. 24, 2022 for EP19193202.9.
European Search Report dated Jan. 28, 2021 for EP20190128.7.
European Search Report dated Feb. 3, 2021 for EP20191283.9.

(56) References Cited

OTHER PUBLICATIONS

European Search Report dated Feb. 12, 2016 for EP13813055.4.
European Search Report dated Feb. 21, 2020 for EP19193202.9.
European Search Report dated Mar. 30, 2016 for EP13838784.0.
European Search Report dated Jun. 16, 2014 for EP14160501.4.
European Search Report dated Aug. 19, 2014 for EP12755426.9.
European Search Report dated Aug. 20, 2019 for EP14774594.7.
European Search Report dated Sep. 6, 2016 for EP14774594.7.
European Search Report dated Oct. 17, 2018 for EP16756335.2.
European Search Report dated Nov. 29, 2021 for EP21165437.1.
European Search Report dated Dec. 6, 2018 for EP13813055.4.
European Search Report dated Dec. 23, 2020 for EP20199088.4.
Extended European Search Report dated Jan. 7, 2022 for EP21181412.4.
Extended European Search Report dated Mar. 30, 2016 for EP13838578.6.
Extended European Search Report dated Jun. 25, 2015 for EP12739348.6.
Extended European Search Report dated Jul. 26, 2016 for EP14741114.4.
International Preliminary Report dated Mar. 24, 2015 for PCT/US2013/060812.
International Preliminary Report dated Jul. 30, 2013 for PCT/US2012/023006.
International Report on Patentability dated Jul. 22, 2014 for PCT/US2013/021554.
International Search Report and Written Opinion dated Mar. 27, 2014 for PCT/US2013/060172.
Notice of Allowance dated Sep. 7, 2022 for U.S. Appl. No. 13/827,790.
Notice of Allowance dated Oct. 4, 2017 for U.S. Appl. No. 14/204,466.
Notice of Allowance dated Oct. 9, 2019 for U.S. Appl. No. 13/826,618.
Notice of Allowance dated Dec. 14, 2020 for U.S. Appl. No. 14/081,715.
Notice of Allowance dated Dec. 15, 2020 for U.S. Appl. No. 15/806,020.
Notice of Allowance dated Dec. 15, 2022 for U.S. Appl. No. 13/742,077.
Office Action dated Jan. 2, 2019 for U.S. Appl. No. 13/360,444.
Office Action dated Jan. 2, 2019 for U.S. Appl. No. 14/152,590.
Office Action dated Jan. 10, 2019 for U.S. Appl. No. 13/826,618.
Office Action dated Jan. 12, 2016 for U.S. Appl. No. 14/152,590.
Office Action dated May 1, 2020 for U.S. Appl. No. 16/035,334.
Office Action dated May 9, 2014 for U.S. Appl. No. 13/360,444.
Office Action dated May 11, 2018 for U.S. Appl. No. 13/826,618.
Office Action dated May 11, 2018 for U.S. Appl. No. 14/832,422.
Office Action dated May 12, 2022 for U.S. Appl. No. 13/827,790.
Office Action dated May 19, 2017 for U.S. Appl. No. 13/742,025.
Office Action dated May 22, 2023 for U.S. Appl. No. 16/877,259.
Office Action dated Jun. 1, 2016 for U.S. Appl. No. 14/134,280.
Office Action dated Jun. 8, 2016 for U.S. Appl. No. 14/044,050.
Office Action dated Jun. 9, 2016 for U.S. Appl. No. 14/152,626.
Office Action dated Jun. 15, 2018 for U.S. Appl. No. 14/207,344.
Office Action dated Jun. 19, 2017 for U.S. Appl. No. 14/081,504.
Office Action dated Jun. 20, 2023 for U.S. Appl. No. 17/068,627.
Office Action dated Jun. 23, 2017 for U.S. Appl. No. 13/829,493.
Office Action dated Jun. 28, 2018 for U.S. Appl. No. 14/081,715.
Office Action dated Jun. 29, 2017 for U.S. Appl. No. 14/081,715.
Office Action dated Jun. 30, 2016 for U.S. Appl. No. 14/081,715.
Office Action dated Jul. 2, 2014 for U.S. Appl. No. 14/044,050.
Office Action dated Jul. 11, 2019 for U.S. Appl. No. 14/081,715.
Office Action dated Jul. 12, 2017 for U.S. Appl. No. 15/053,232.
Office Action dated Jul. 13, 2018 for U.S. Appl. No. 13/827,790.
Office Action dated Jul. 26, 2017 for U.S. Appl. No. 13/827,790.
Office Action dated Jul. 26, 2018 for U.S. Appl. No. 14/152,590.
Office Action dated Jul. 29, 2015 for U.S. Appl. No. 14/152,626.
Office Action dated Jul. 30, 2020 for U.S. Appl. No. 15/806,020.
Office Action dated Aug. 5, 2021 for U.S. Appl. No. 13/827,790.
Office Action dated Aug. 6, 2018 for U.S. Appl. No. 13/360,444.
Office Action dated Aug. 7, 2019 for U.S. Appl. No. 15/806,020.
Office Action dated Aug. 10, 2015 for U.S. Appl. No. 14/044,050.
Office Action dated Aug. 22, 2019 for U.S. Appl. No. 14/207,344.
Office Action dated Aug. 29, 2014 for U.S. Appl. No. 14/152,590.
Office Action dated Sep. 9, 2016 for U.S. Appl. No. 14/081,504.
Office Action dated Sep. 9, 2016 for U.S. Appl. No. 14/207,344.
Office Action dated Sep. 11, 2017 for U.S. Appl. No. 14/832,422.
Office Action dated Sep. 23, 2016 for U.S. Appl. No. 14/152,590.
Office Action dated Sep. 24, 2014 for U.S. Appl. No. 14/031,746.
Office Action dated Sep. 27, 2016 for U.S. Appl. No. 13/827,790.
Office Action dated Sep. 28, 2017 for U.S. Appl. No. 14/207,344.
Office Action dated Oct. 6, 2016 for U.S. Appl. No. 13/360,444.
Office Action dated Oct. 6, 2016 for U.S. Appl. No. 13/742,025.
Office Action dated Oct. 7, 2019 for U.S. Appl. No. 13/360,444.
Office Action dated Oct. 7, 2019 for U.S. Appl. No. 14/152,590.
Office Action dated Oct. 10, 2014 for U.S. Appl. No. 13/742,025.
Office Action dated Oct. 15, 2015 for U.S. Appl. No. 13/827,790.
Office Action dated Oct. 20, 2017 for U.S. Appl. No. 13/826,618.
Office Action dated Oct. 26, 2016 for U.S. Appl. No. 13/742,077.
Office Action dated Nov. 2, 2015 for U.S. Appl. No. 13/742,077.
Office Action dated Nov. 9, 2022 for U.S. Appl. No. 16/877,259.
Office Action dated Nov. 17, 2016 for U.S. Appl. No. 13/829,493.
Office Action dated Nov. 17, 2017 for U.S. Appl. No. 13/360,444.
Office Action dated Nov. 18, 2016 for U.S. Appl. No. 13/826,618.
Office Action dated Nov. 20, 2015 for U.S. Appl. No. 13/826,618.
Office Action dated Nov. 21, 2017 for U.S. Appl. No. 14/152,590.
Office Action dated Dec. 18, 2015 for U.S. Appl. No. 14/081,504.
Office Action dated Dec. 23, 2020 for U.S. Appl. No. 13/827,790.
Office Action dated Dec. 24, 2021 for U.S. Appl. No. 16/877,259.
Office Action dated Dec. 28, 2017 for U.S. Appl. No. 13/827,790.
Office Action dated Dec. 29, 2017 for U.S. Appl. No. 14/081,504.
Arras, et al., "Electrospinning of Aligned Fibers with Adjustable Orientation Using Auxiliary Electrodes", Sci. Technol. Adv. Mater., 13, Jan. 1, 2012 00:00:00.0.
Yasuda, et al., "Contact Angle of Water on Polymer Surfaces", Am Chem, Langmuir, vol. 10 No. 7, Jan. 1, 1994 00:00:00.0.
European Search Report dated Nov. 5, 2024 for EP19193202.9.
European Search Report dated Dec. 13, 2024 for EP22760630.8.
Final Office Action dated Nov. 5, 2024 for U.S. Appl. No. 16/877,259.
International Search Report and Written Opinion dated Sep. 17, 2013 for PCT/US2013/060172.
Office Action dated Jan. 16, 2025 for U.S. Appl. No. 18/170,364.
Office Action dated Oct. 22, 2024 for U.S. Appl. No. 16/895,975.
Office Action dated Oct. 23, 2024 for U.S. Appl. No. 16/896,013.
Notice of Allowance dated Feb. 27, 2025 for U.S. Appl. No. 16/877,259.
Office Action dated Feb. 14, 2025 for U.S. Appl. No. 17/068,627.
Office Action dated Mar. 5, 2025 for U.S. Appl. No. 17/341,038.
European Examination Report dated Mar. 24, 2025 for EP21189728.5.
European Examination Report dated Apr. 8, 2025 for EP21181412.4.
Notice of Allowance dated Apr. 10, 2025 for U.S. Appl. No. 16/877,259.
Office Action dated Apr. 10, 2025 for U.S. Appl. No. 17/515,236.

\* cited by examiner

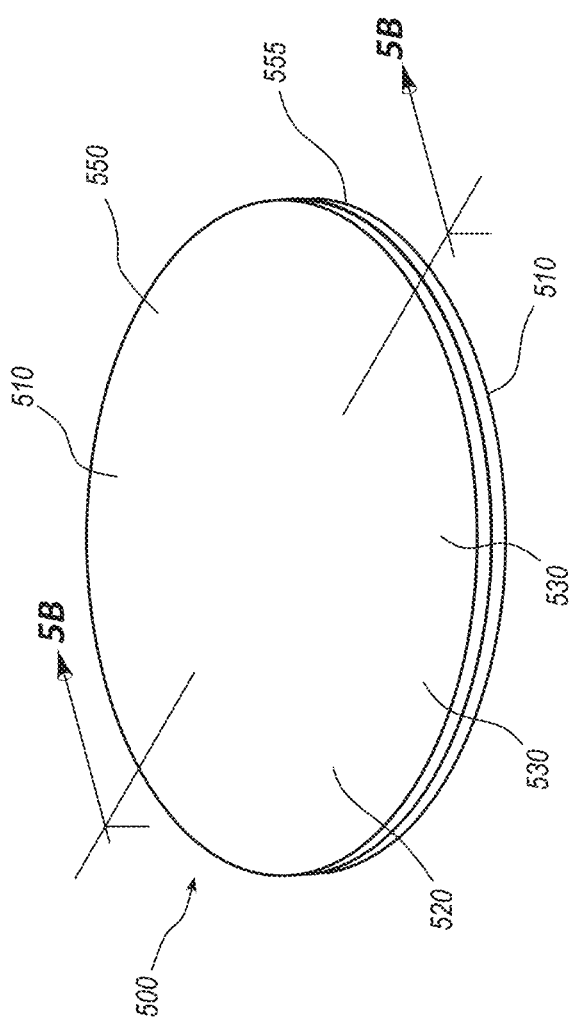
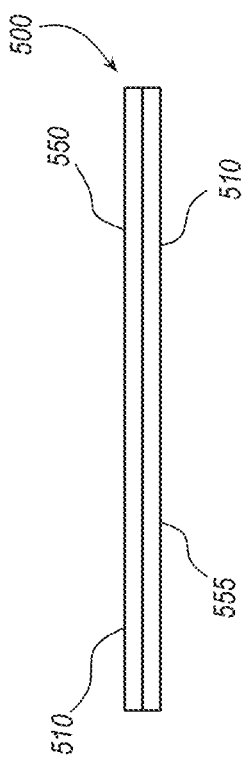
FIG. 5A
FIG. 5B

FIBROUS CONSTRUCTS WITH THERAPEUTIC MATERIAL PARTICLES

RELATED APPLICATIONS

This application claims priority to U.S. Provisional Application No. 63/154,288, filed on Feb. 26, 2021 and titled, "Fibrous Constructs with Carbon Material Particles," which is hereby incorporated by reference in its entirety.

TECHNICAL FIELD

The present disclosure relates generally to fibrous sheets that may be used as part of a medical device. In some embodiments, the fibrous sheets may include micro or nano fibers made of a composite of a polymer matrix and micro particles, including carbon material particles, including graphene. In certain embodiments, the fibrous sheets may be in a form of a tube. The disclosure also relates to devices, such as covered stents, vascular grafts, wound dressings, pledgets, filters, personal protective equipment, such as drapes, shields, masks, and respirators, filters for air and water, separation membranes for batteries and fuel cells.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A is a schematic detail view of a section 1A of the sheet of FIG. 1.

FIG. 1B is a cross-sectional view of a fiber of FIG. 1 having a coating of carbon material particles.

FIG. 2A is a schematic detail view of a section 2A of the sheet of FIG. 2.

FIG. 5A is a perspective view of a schematic representation of a fibrous membrane.

FIG. 5B is a side view of the membrane of FIG. 5A.

DETAILED DESCRIPTION

Figure 1:
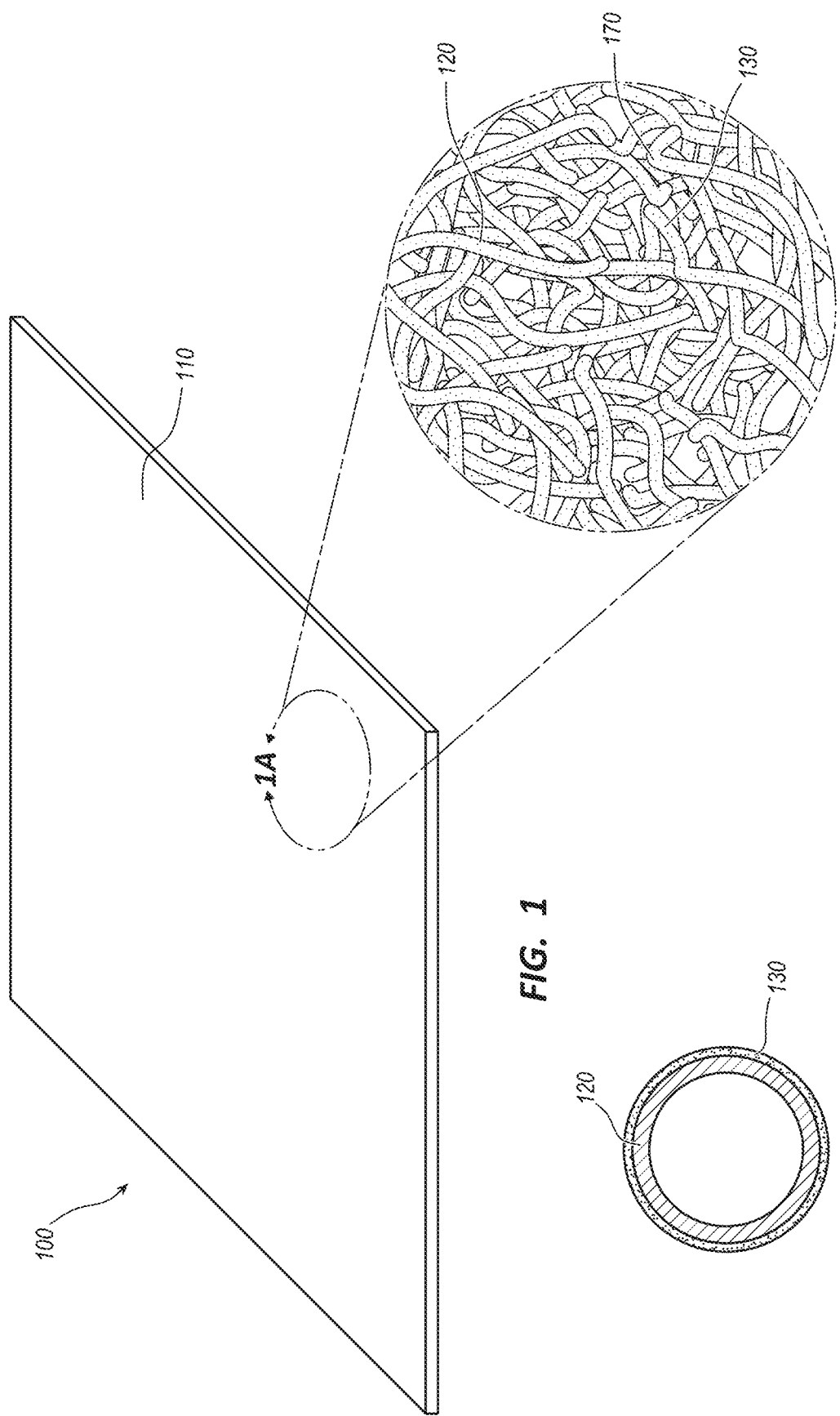
FIG. 1 is a perspective view of a schematic representation of an embodiment of a fibrous sheet including fibers having carbon material particles.

A variety of medical treatments or diagnostics may be performed by inserting and/or implanting medical devices into the circulatory system, tissues, or other body lumens of a patient. For example, medical devices that may be used for the treatment of vascular disease include stents, catheters, balloon catheters, guide wires and cannulas. In some instances, the use of inserted and/or implanted medical devices may cause undesired complications such as injury to the endothelium and to smooth muscle cells in the vasculature, which can result in thrombus deposition, inflammation, leukocyte and macrophage infiltration, smooth muscle cell proliferation/migration, restenosis, fibrosis, and extracellular matrix deposition. Moreover, the use of insertable and/or implantable medical devices can lead to neointimal growth and lumen compromise.

A coating on a medical device may be configured to inhibit or reduce inflammatory responses by the body in response to the device. For example, a medical device configured to permit tissue ingrowth and/or the growth or attachment of endothelial cells onto blood contacting surfaces of the device may reduce the likelihood of negative flow characteristics and thrombosis formation. Similarly, a device so configured may mitigate the body's inflammatory response toward the material on, for example, the tissue or non-blood contacting surfaces of the device. Such a coating may include a surface comprising micro particles configured to reduce or inhibit inflammation or tissue injury, tissue proliferation, infection, or thrombosis that may result from the presence of the device. The coating may also be configured to increase wound healing or vessel occlusion caused by thrombosis.

Disclosed herein are fibrous sheets that may be configured to reduce an inflammatory biologic response. The fibrous sheets may include a mat of micro or nano fibers having a polymer matrix. The fibers may include carbon material particles or micro particles or a combination of the two. In some embodiments, the polymer matrix comprises polytetrafluoroethylene (PTFE). Furthermore, embodiments wherein the fibers are formed by processes such as rotational spinning, electrospinning, or pressure extrusion and stretching are all within the scope of this disclosure. Accordingly, fibrous sheets comprising rotational spun fibers (including rotational spun PTFE fibers), electrospun fibers (including electrospun PTFE fibers), and fibers formed by stretching (including fibrous membranes comprising expanded PTFE (ePTFE)) are within the scope of this disclosure. Thus, the term fiber as used herein is broad enough to include serially deposited fibers created by processes such a rotational spinning and electrospinning as well as fibers formed by stretching processes, such as the fibers or fibrils that comprise the node and fibril structure of ePTFE. Carbon material particles within the scope of this disclosure include graphene and/or pyrolytic carbon particles. Furthermore, the micro particles may include elemental metal, metal oxides, metal colloids, etc. In some instances, the fibrous sheet may be used as a portion of an implanted vascular medical device, as a portion of a wound dressing, as a filter media, and so on.

Additionally, membranes or sheets within the scope of this disclosure may be used on the outside of the body as dressings, bandages, or other products. A coating on these sheets may be configured to inhibit inflammatory or infection response during wound healing. Sheets or membranes within the scope of this disclosure may also be used to cover the mouth, nose, and face to prevent respiratory contamination with particulate, bacteria or viruses. Still further, sheets or membranes within the scope of this disclosure may be used in surgical drapes to prevent microbial and/or viral contamination and proliferation during medical procedures. Still further, sheets or membranes within the scope of this disclosure may be bactericidal and/or viricidal.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

In other instances, an external medical device may be used to treat or diagnose a patient. For example, a wound dressing may be placed over an external wound to facilitate protecting and healing of the wound.

The phrase "coupled to" refers to any form of interaction between two or more entities, including chemical, mechanical, electrical, magnetic, electromagnetic, fluid, and thermal interaction. Two components may be coupled to each other even though they are not in direct contact with each other. For example, two components may be coupled to each other through an intermediate component.

The terms, "additive," "micro particle," "carbon material particle," and other related terms may be used interchangeably herein. An additive may be used singly or in combination with other additives.

FIGS. 1-8B illustrate different views and representations of a fibrous sheets and devices comprising such fibrous sheets. In certain views each fibrous sheet or device may be coupled to, or shown with, additional components or layers not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1-1A illustratively depict an embodiment of a fibrous sheet 100. In the illustrated embodiment, the fibrous sheet 100 is partially comprised of a mat 110. The mat 110 may be formed of a plurality of micro or nano fibers 120 intertwined together to form a porous microstructure. A thickness of the mat 110 may range from about 5 microns to about 100 microns. A diameter of the fibers 120 may range from about 0.25 micron to about 1.75 micron. The fibrous sheet 100 may be utilized in the construction of various medical appliances, such as facemasks, surgical drapes, dressings, bandages, vascular prostheses, filter membranes, etc.

The fibers 120 may be formed of a composite material including a polymer matrix 170 and a plurality of carbon material particles 130. The polymer matrix 170 may include any suitable polymer material that can be extruded into the fibers 120 using rotational spinning, electrospinning, or pressure extrusion and stretching techniques. In some embodiments, the polymers used may be configured to withstand sintering temperatures of between 360° C. and 400° C. For example, the polymer matrix 170 may include PTFE, nylon 6-6, poly paraphenylene terephthalamide, polyurethane, polyethylene, poly(vinyl alcohol, or polypropylene.

In certain embodiments, fibers comprising additive particles may be produced through a rotational spinning process. For example, a flowable polymer (e.g., a PTFE dispersion or other polymer solution) and an additive material (such as graphene particles, a graphene dispersion, or pyrolytic carbon) may be loaded into a cup or spinneret configured with orifices on an outside circumference of the spinneret. Processes where a flowable polymeric mixture is formed into fibers as it is expelled from a rotating surface without orifices are likewise within the scope of this disclosure. In embodiments with orifices, the orifices may be 29 ga or 30 ga needles. The solution or dispersion may include from about 5 wt % to about 70 wt % polymer and from about 60 wt % to about 70 wt %; and from about 0.05 wt % to about 15 wt %, from about 1 wt % to about 5 wt %, and from about 0.1 wt % to about 0.2 wt % additive particles. The spinneret is then rotated at a rate of about 5500 rpm to about 6500 rpm for about three minutes, causing (through a combination of centrifugal and hydrostatic forces, for example) the material within the cup or spinneret to be expelled from the orifices. The material may then form a "jet" or "stream" extending from the orifice, with drag forces tending to cause the stream of material to elongate into a small diameter fiber. The fibers may then be directly deposited on a collection apparatus to form a sheet. In some instances, and with some materials, the sheet may then be sintered, for example at a temperature between about 360° C. and about 400° C. and about 385' C for about 8 min. In some embodiments, the rotational spinning process is completed in the absence of an electrical field. Exemplary methods and systems for rotational spinning can be found in U.S. Patent Publication No. US2009/0280325, titled "Methods and Apparatuses for Making Superfine Fibers," which is incorporated herein by reference in its entirety.

In certain embodiments, fibers comprising additive particles may be produced through an electrospinning process. For example, a flowable polymer (e.g., a PTFE dispersion or other polymer solution) and an additive material (such as graphene particles, a graphene dispersion, or pyrolytic carbon) may be loaded into a syringe pump or other device configured to expel the materials through an orifice. The solution or dispersion may include from about 5 wt % to about 70 wt % polymer and from about 0.05 wt % to about 1.0 wt % additive particles. The solution is dispensed from the orifice at a controlled rate and electrostatic forces are used to draw the expelled material to a collection device. The electrostatic force can be about 1.5 kV. The material may then form a "jet" or "stream" extending from the orifice. In some instances, the orifice or solution may be charged and an opposite electrical charge is applied to the collection surface such that a difference in electrical charge causes the stream of material to elongate into a small diameter fiber 120. The fibers 120 may then be directly deposited on the collection apparatus that is about seven inches from the orifice. to form the mat 110. For some materials, the mat 110 may then be sintered at a temperature between about 360° C. and about 400° C. and about 385° C. for about 8 min. Electrospinning is described in U.S. patent application Ser. No. 13/360,444, titled "Electrospun PTFE Coated Stent and Method of Use," which is herein incorporated by reference in its entirety.

In some embodiments, a pressure extrusion and stretching process may comprise the steps of: (a) mixing a polymer at a concentration of from about 70 wt % to about 95 wt %, a lubricating agent at a concentration of from about 5 wt % to about 30 wt %, such that a lube/polymer ratio ranges from about 5% to about 30% and the additive particles (such as graphene particles, a graphene dispersion, or pyrolytic carbon) at a concentration of from about 0.01 wt % to about 5% to form a solution or dispersion; (b) forming a billet comprising the solution or dispersion; (c) extruding the billet under a pressure of about 300 lbf to about 60,000 lbf at a rate of about 0.01 inch/min to about 10 inch/min and at a temperature of about 21 degrees C. to about 70 degrees C. to form a tape; (d) drying the tape to facilitate evaporation of the lubricating agent; (e) calendaring the tape using chilled, room temperature, or heated rolls ranging from −50 C to 300 C (f) tentering the tape to uniaxially or biaxially stretch it in a first direction at about one inch/sec to about 30 inches/sec to about 110% to about 600% elongation and/or a second direction perpendicular to the first direction to form nodes and fibrils; and/or stretching the material in one or more directions through other processes; and (f) sintering the material, for example at a temperature between about 360° C. and about 400° C.

A "polymeric mixture" as used herein includes mixtures of polymeric materials and carbon or other particles that can be formed into fibers via rotational spinning, electrospinning, pressure extrusion and stretching, and/or other processes. Polymeric dispersions, including aqueous dispersions, and/or polymeric powders can be combined with carbon or other particles to create polymeric mixtures within the scope of this disclosure.

The carbon material particles 130 may include a variety of materials, including materials formed of only carbon atoms. For example, the carbon material particles 130 may include graphene nanosheets, graphene quantum dots, graphene nanoribbons, graphene nanoparticles, graphene oxides, pyrolytic carbon, carbon nanofibers, carbon nanotubes, fullerenes, mesoporous carbon, graphite, pyrolytic graphite or any combination thereof. Each of the carbon material particles 130 may have a maximum dimension of less than about 0.159 mm. In other words, a dimension of width, length, thickness, or diameter may not exceed 0.159 mm. This configuration allows the carbon material particles 130 to pass through an orifice having a maximum diameter of 0.159 mm during an extrusion process to form the fibers 120. In certain embodiments, the maximum dimension of each of the carbon material particles 130 may range from about 0.01 μm to about 50 μm such that the carbon material particles 130 may be integrated into the fibers 120.

As an element of a medical device, the carbon material particles 130 may have beneficial functions such as an anti-thrombogenic, anti-proliferative tissue response, anti-microbial, anti-viral, protein biofunctionalization, DNA biofunctionalization, facilitation of gene or small molecule drug delivery, cancer treatment, and biosensors. In certain embodiments the carbon material particles 130 may be dispersed throughout the polymer matrix 170 of the fiber 120, including exposed at a surface of the fiber 120 and retained by the polymer matrix 170 such that the carbon material particles 130 are not eluted into a surrounding environment. The carbon material particles 130 disposed at the surface of the fiber 120 may interact with cells or substances in the surrounding environment. In other embodiments, the carbon material particles 130 may be concentrated adjacent the surface of the fiber 120 and retained by the polymer matrix 170 such that the carbon material particles 130 are not eluted into the surrounding environment. In some embodiments, the carbon material particles 130 may completely cover the surface of the fiber 120 such that the carbon material particles 130 form a coating, as shown in FIG. 1B. In another embodiment, the carbon material particles 130 can be larger than a diameter of the fiber 120. In this embodiment, the carbon material particles 130 can be adhered to or entangled by the fibers 120 to retain the carbon material particles 130 within the mat 110.

Figure 2:
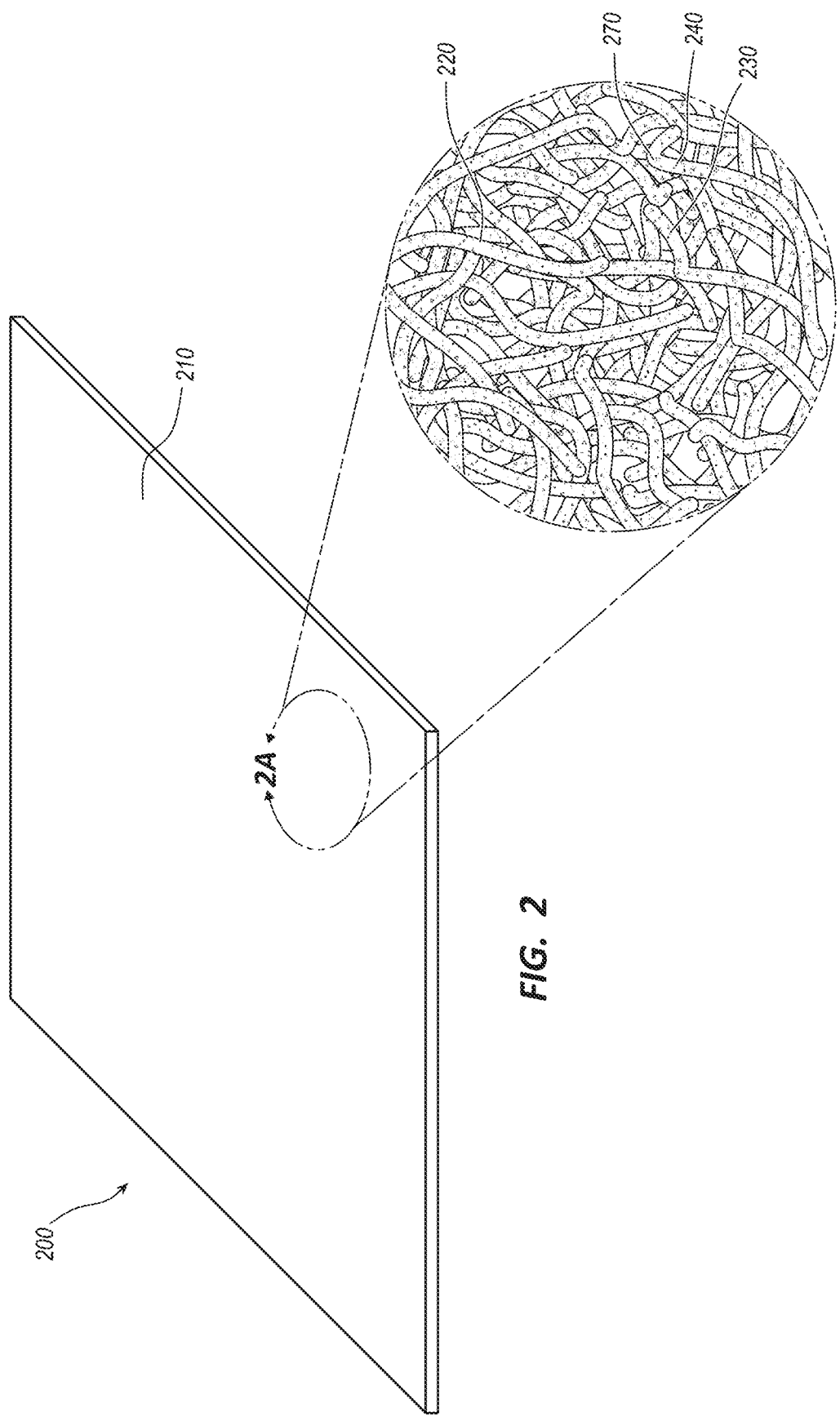
FIG. 2 is a perspective view of a schematic representation of an embodiment of a fibrous sheet including fibers having carbon material particles and micro particles.

FIGS. 2-2A illustratively depict an embodiment of a fibrous sheet 200 that resembles the fibrous sheet 100 described above in certain respects. Accordingly, like features are designated with like reference numerals, with the leading digit incremented to "2." For example, the embodiment depicted in FIGS. 2-2A includes a mat 210 that may, in some respects, resemble the mat 110 of FIG. 1. Relevant disclosure set forth above regarding similarly identified features thus may not be repeated hereafter. Moreover, specific features of the fibrous sheet 100 and related components shown in FIGS. 1-1A may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the fibrous sheet 200 and related components depicted in FIGS. 2-2A. Any suitable combination of the features, and variations of the same, described with respect to the fibrous sheet 100 and related components illustrated in FIGS. 1-1A can be employed with the fibrous sheet 200 and related components of FIGS. 2-2A, and vice versa. This pattern of disclosure applies equally to further embodiments depicted in subsequent figures and described hereafter, wherein the leading digits may be further incremented.

FIGS. 2-2A depict another embodiment of a fibrous sheet 200. In the illustrated embodiment, the fibrous sheet 200 is partially comprised of a mat 210. The mat 210 may be formed of a plurality of micro or nano fibers 220 intertwined together to form a porous microstructure. The fibers 220 may be formed of a composite material including a polymer matrix 270, a plurality of carbon material particles 230, and a plurality of micro particles 240. The polymer matrix 270 may include any suitable polymer material that can be dispersed into a dispersion or solution and extruded into the fibers 220 using rotational spinning, electrospinning, or pressure extrusion and stretching techniques as described above.

The polymer material, carbon material particles 230, and therapeutic micro particles 240 may be mixed together to form an extrudable solution or dispersion. The concentration of the polymer may be from about 5 wt % to about 70 wt %. The concentration of the graphene flakes may be from about 0.05 wt % to about 1.0 wt %. The concentration of the micro particles 240 may be from about 0.05 wt % to about 15 wt %. Each of the particles 230, 240 may have a maximum dimension of less than about 0.159 mm. In other words, a dimension of width, length, thickness, or diameter may not exceed 0.159 mm. This configuration allows the particles 230, 240 to pass through an orifice having a maximum diameter of 0.159 mm during an extrusion process to form the fibers 220. In certain embodiments, the maximum dimension of each of the particles 230, 240 may range from about 0.01 µm to about 5 µm such that the particles 230, 240 may be integrated into the fibers 220.

The micro particles 240 may include any suitable substance that facilitates treatment of a patient or filtration of a fluid. For example, the micro particles 240 may facilitate thrombosis, wound healing, non-cell adhesion, death or inhibition of pathogens (e.g., microbes), drug delivery, cancer treatment, etc. Exemplary substances may be elemental metal, metal oxide, metal colloidal, pyrolytic carbon, poly paraphenylene terephthalamide, polyamid, potassium ferrate, and calcium phosphate. Other substances are within the scope of this disclosure.

Examples of the elemental metal substance may include noble metals, such as silver, gold, platinum, rhodium, iridium, palladium, ruthenium, and osmium which may have an antimicrobial function. Examples of suitable metal colloids may include silver colloid, copper colloid, platinum colloid, etc.

Examples of suitable metal oxides may include copper(I) oxide ($Cu_2O$); silver(I) oxide ($Ag_2O$); thallium oxide ($Tl_2O$); sodium oxide ($Na_2O$); aluminum monoxide (AlO); barium oxide (BaO); beryllium oxide (BeO); cadmium oxide (CdO); calcium oxide (CaO); cobalt(II) oxide (CoO); copper(II) oxide (CuO); iron(II) oxide (FeO); magnesium oxide (MgO); mercury(II) oxide (HgO); nickel(II) oxide (NiO); palladium(II) oxide (PdO); silver(II) oxide (AgO); strontium oxide (SrO); tin(II) oxide (SnO); titanium(II) oxide (TiO); vanadium(II) oxide (VO); zinc oxide (ZnO); aluminum oxide ($Al_2O_3$); antimony trioxide ($Sb_2O_3$); bismuth trioxide ($Bi_2O_3$); chromium(III) oxide ($Cr_2O_3$); erbium(III) oxide ($Er_2O_3$); gadolinium(III) oxide ($Gd_2O_3$); gallium(III) oxide ($Ga_2O_3$); holmium(III) oxide ($Ho_2O_3$); indium(III) oxide($In_2O_3$); iron(III) oxide ($Fe_2O_3$); lanthanum(III) oxide ($La_2O_3$); lutetium(III) oxide ($Lu_2O_3$); nickel (III) oxide ($Ni_2O_3$); promethium(III) oxide ($Pm_2O_3$); rhodium(III) oxide ($Rh_2O_3$); samarium(III) oxide ($Sm_2O_3$); scandium(III) oxide ($Sc_2O_3$); terbium(III) oxide ($Tb_2O_3$); thallium(III) oxide ($Tl_2O_3$); thulium(III) oxide ($Tm_2O_3$); titanium(III) oxide ($Ti_2O_3$); tungsten(III) oxide ($W_2O_3$); vanadium(III) oxide ($V_2O_3$); ytterbium(III) oxide ($Yb_2O_3$); yttrium(III) oxide ($Y_2O_3$); cerium(IV) oxide ($CeO_2$); chromium(IV) oxide ($CrO_2$); germanium dioxide ($GeO_2$); hafnium(IV) oxide ($HfO_2$); manganese(IV) oxide ($MnO_2$); plutonium dioxide ($PuO_2$); ruthenium(IV) oxide ($RuO_2$); thorium dioxide ($ThO_2$); tin dioxide ($SnO_2$); titanium dioxide ($TiO_2$); tungsten(IV) oxide ($WO_2$); vanadium(IV) oxide ($VO_2$); zirconium dioxide ($ZrO_2$); antimony pentoxide ($Sb_2O_5$); tantalum pentoxide ($Ta_2O_5$); vanadium(V) oxide ($V_2O_5$); chromium trioxide ($CrO_3$); molybdenum(VI) oxide ($MoO_3$); rhenium trioxide ($ReO_3$); tungsten trioxide ($WO_3$); manganese(VII) oxide ($Mn_2O_7$); rhenium(VII) oxide ($Re_2O_7$); osmium tetroxide ($OsO_4$); ruthenium tetroxide ($RuO_4$); and permutations and combinations of those (and other) metal oxides.

In certain embodiments the particles 230, 240 may be dispersed throughout the polymer matrix 270 of the fiber 220, including exposed at a surface of the fiber 220 and retained by the polymer matrix 270 such that the particles 230, 240 are not eluted into a surrounding environment. The particles 230, 240 disposed at the surface of the fiber 220 may interact with cells or substances in the surrounding environment. In other embodiments, the particles 230, 240 may be concentrated adjacent the surface of the fiber 220 and retained by the polymer matrix 270 such that the particles 230, 240 are not eluted into the surrounding environment.

Figures 3, 3A:
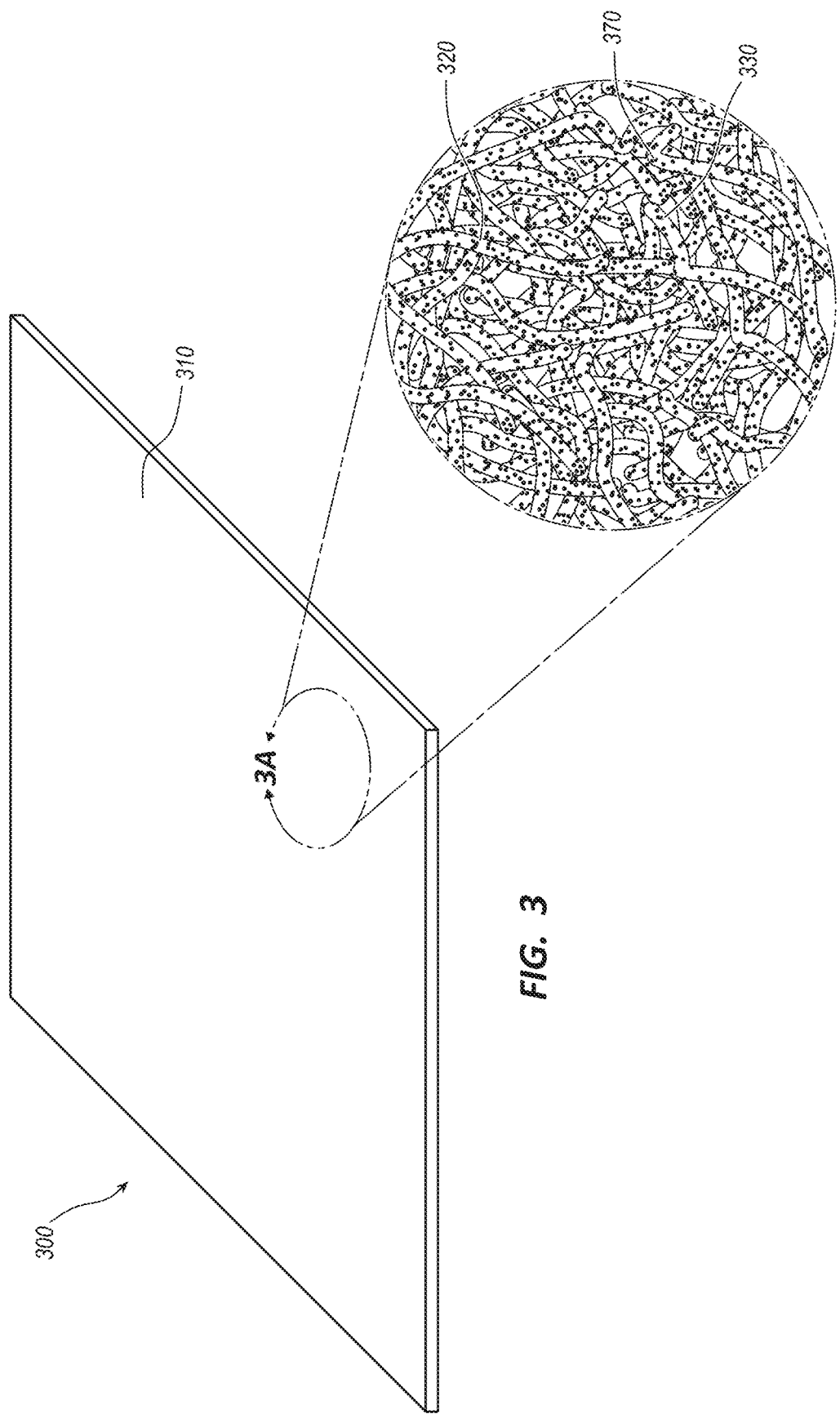
FIG. 3 is a perspective view of a schematic representation of an embodiment of a fibrous sheet including fibers having micro particles.
FIG. 3A is a schematic detail view of a section 3A of the sheet of FIG. 3.

FIGS. 3-3A illustratively depict another embodiment of a fibrous sheet 300. In the illustrated embodiment, the fibrous sheet 300 is partially comprised of a mat 310. The mat 310 may be formed of a plurality of micro or nano fibers 320 intertwined together to form a porous microstructure as illustrated in FIG. 3A. The fibers 320 may be formed of a composite material including a polymer matrix 370 and a plurality of therapeutic micro particles 340. The polymer matrix 370 may include any suitable polymer material that can be dispersed into a dispersion or solution and extruded into the fibers 320 using rotational spinning, electrospinning, or pressure extrusion and stretching techniques as described above.

The polymer material and micro particles 340 may be mixed together to form an extrudable solution or dispersion. The micro particles 340 may comprise any suitable substance as previously discussed. The concentration of the polymer material may be from about 70 wt % to about 95 wt %. The concentration of the micro particles 340 may be from about 0.01 wt % to about 5 wt %. Each of the micro particles 340 may have a maximum dimension of less than about 0.159 mm. In other words, a dimension of width, length, thickness, or diameter may not exceed 0.159 mm. This configuration allows the micro particles 340 to pass through an orifice having a maximum diameter of 0.159 mm during an extrusion process to form the fibers 320. In certain embodiments, the maximum dimension of each of the micro particles 340 may range from about 0.01 µm to about 50 µm such that the micro particles 340 may be integrated into the fibers 320.

In certain embodiments, the micro particles 340 may be dispersed throughout the polymer matrix 370 of the fiber 320, including exposed at a surface of the fiber 320 and retained by the polymer matrix 370 such that the micro particles 340 are not eluted into a surrounding environment. The micro particles 340 disposed at the surface of the fiber 320 may interact with cells or substances in the surrounding environment. In other embodiments, the micro particles 340 may be concentrated adjacent the surface of the fiber 320 and retained by the polymer matrix 370 such that the micro particles 340 are not eluted into the surrounding environment.

In other embodiments, any one of the fibers 120, 220, 320 may be fully coated with any one or any combination of the particles 140, 330, 240, 340 such that the polymer matrix 170, 270, 370 is not exposed to an external environment.

Figure 4A:
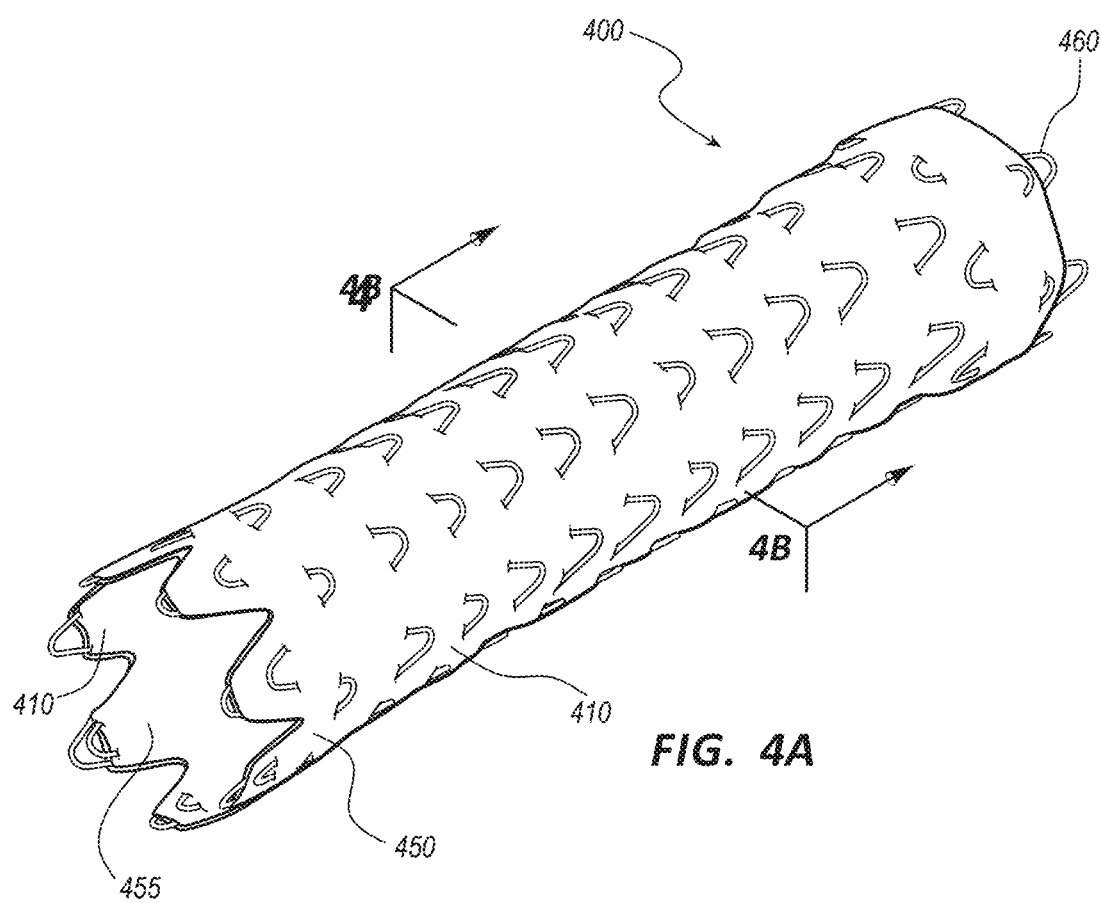
FIG. 4A is a perspective view of an embodiment of a covered stent.
Figure 4B:
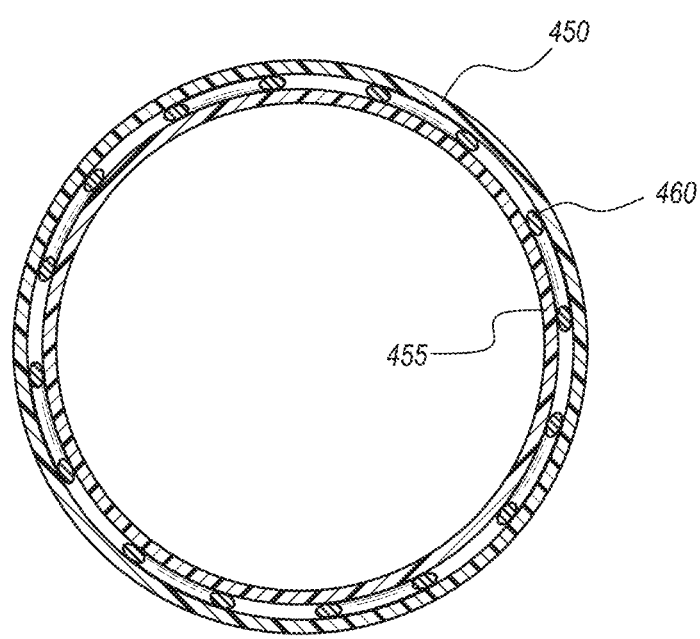
FIG. 4B is a cross-sectional view of the covered stent of FIG. 4A taken through plane 4B-4B.

FIGS. 4A-4B depict an embodiment of a covered stent 400 which is configured to maintain patency of a blood vessel. As shown in the illustrated embodiment, the covered stent 400 comprises a first or inner layer 455 and a stent 460 surrounding the first layer 455. The covered stent 400 may further comprise a second or outer layer 450 surrounding the first layer 455 and the stent 460. In certain embodiments, the covered stent 400 may include other layers sandwiched between the first layer 455 and the second layer 450. The first layer 455 and the second layer 450 may be partially comprised of mats 410, 410a, respectively. The mats 410, 410a may be similar to any of the previously described mats 110, 210, 310. Other embodiments of the mats 410, 410a are within the scope of this disclosure. The mat 410 of the first layer 455 may have similar characteristics (e.g., porosity, fiber size, fiber material, and additives) as the mat 410a of the second layer 450. In other embodiments, the mats 410, 410a may differ in characteristics to exhibit different functionality dependent upon an intended use of the covered stent 400. For example, the mat 410 may be in contact with blood and may include an additive that prevents thrombosis while the mat 410a may be in contact with endothelial cells and may include an additive that prevents proliferation of the endothelial cells. In the illustrated embodiment, the mats 410, 410a are formed into tubular structures.

In other embodiments, any of the fibrous sheets 100, 200, 300 may be incorporated into any suitable medical device. For example, the fibrous sheets 100, 200, 300 may be utilized to form a wound dressing. The fibrous sheets 100, 200, 300 may include fibers formed from a polymer and additives such as graphene flakes and/or micro particles 240, 340 that interact with injured tissue to promote healing. In another embodiment, the fibrous sheets 100, 200, 300 may be formed into pledgets. The fibrous sheets 100, 200, 300 may include a polymer and additives such as graphene flakes and/or micro particles that are thrombogenic such that when the pledgets are injected into a blood vessel, the blood vessel clots to prevent blood flow.

FIGS. 5A-5B illustrate a fibrous membrane 500. The fibrous membrane 500 includes a mat 510 which may be similar to any of the previously disclosed mats 110, 210. The fibrous membrane 500 may include a single mat 510. In other embodiments, the fibrous membrane 500 may include 2, 3, 4, 5, or more mats 510 stacked together. Each mat 510 may have similar characteristics (e.g., porosity, fiber material, and additives) as an adjacent mat 510. In another embodiment, each mat 510 may have different characteristics than an adjacent mat 510. The fibrous membrane 500 may be utilized as a filter for any type of fluid, such as water and air. The porosity and large surface area of the fibrous membrane 500 provides good filtering capabilities.

In certain embodiments, the fibrous membrane 500 may be self-cleaning. For example, the fibrous membrane 500 may be utilized to filter contaminants from a fluid. The contaminants may adhere to a surface 520 of the fibrous membrane 500. A voltage may be applied to the fibrous membrane 500. The voltage may be conducted through the fibrous membrane 500. In a certain embodiment, the voltage may heat and burn or char the contaminants such that the fibrous membrane 500 is cleaned of contamination. In another embodiment, the voltage may be positive or negative and charge the fibrous membrane such that contaminants are attracted to the fibrous membrane 500 during a filtration procedure. Following the filtration procedure, the voltage may be reversed such that the fibrous membrane has an opposite charge and the contaminants are expelled from the fibrous membrane 500 such that the fibrous membrane 500 is substantially clean of contamination.

EXAMPLES

A number of exemplary rotational spun sheets were produced according to the disclosure herein. FIGS. 6A-8A are scanning electron micrographs (SEMs) of portions of the rotational spun sheets produced in exemplary processes. The following examples are intended to further illustrate exemplary embodiments and are not intended to limit the scope of the disclosure.

Example 1

A rotational spun sheet is formed. 0.25 g of pyrolytic carbon powder having a particle size of <50 μm is added to 2 ml of water and 0.7 g of poly(ethylene oxide) (PEO). 12 g of 60 wt % dispersion of a PTFE dispersion is added to the dispersion. The mixture can be placed on a roller at a for about 24 hours. Alternatively, the mixture can be hand mixed with a spatula. The mixture is placed in a spinneret with 29 ga or 30 ga needles or orifices and rotational spun at 5500-6500 rpm for three minutes. The expelled fibers are collected and sintered at 385° C. for about eight minutes.

Figure 6A:
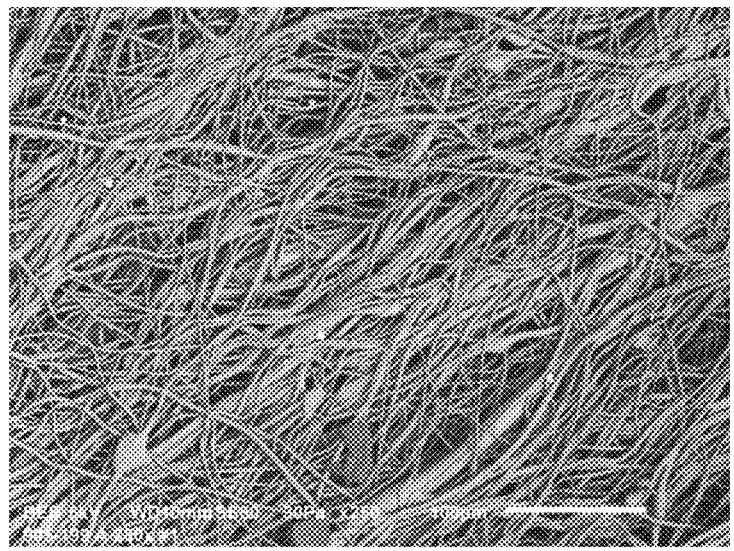
FIG. 6A is a scanning electron micrograph at 250X of a portion of a fibrous sheet.
Figure 6B:
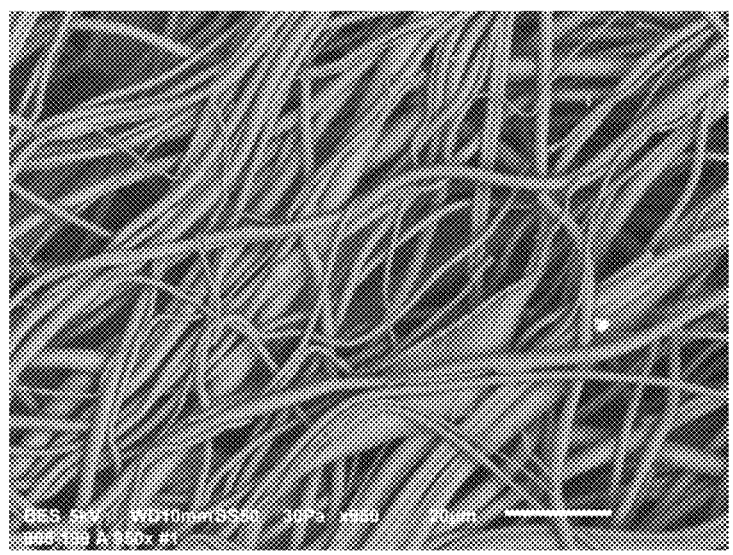
FIG. 6B is a scanning electron micrograph at 950X of a portion of the fibrous sheet of FIG. 6A.

FIG. 6A shows a SEM of a portion of the sheet formed by a rotational spinning process magnified at 250× and FIG. 6B shows the same portion magnified at 950×.

Example 2

An electrospun sheet is formed. 0.53 g 4 wt % graphene oxide powder having a particle size of <10 μm is added to a dispersion of 10 ml of water and 0.7 g of poly(ethylene oxide) (PEO). The mixture can be placed on a roller at a for about 24 hours. Alternatively, the mixture can be hand mixed with a spatula. The mixture is placed in a spinneret with 29 ga or 30 ga needles or orifices and electrospun for ten to twenty minutes with an electrical charge of 1.5 kV and a distance of seven inches to the collector. The expelled fibers are collected and sintered at 385° C. for about eight minutes.

Figure 7A:
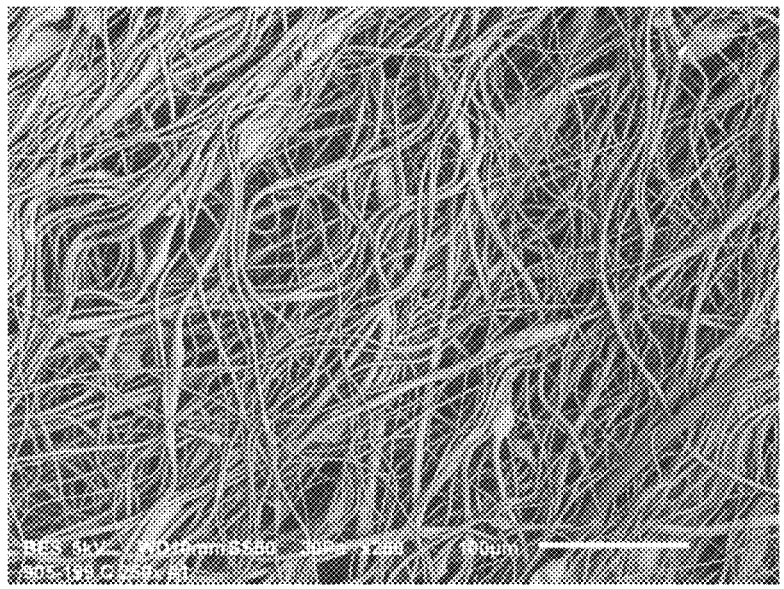
FIG. 7A is a scanning electron micrograph at 250X of a portion of another fibrous sheet.
Figure 7B:
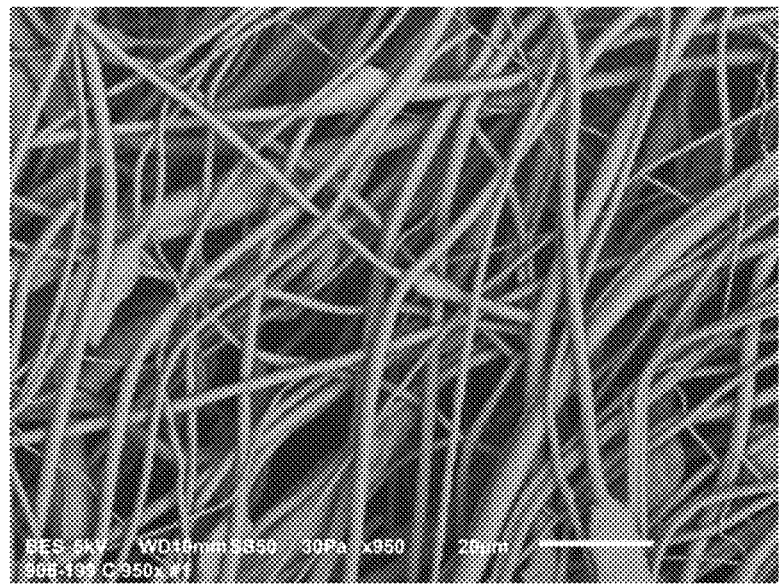
FIG. 7B is a scanning electron micrograph at 950X of a portion of the fibrous sheet of FIG. 7A.

FIG. 7A shows a SEM of a portion of the sheet formed by an electrospinning process magnified at 250× and FIG. 7B shows the same portion magnified at 950×.

Example 3

A rotational spun sheet is formed. 0.25 g of pyrolytic carbon powder having a particle size of <50 μm is added to 2 ml of water and 0.7 g of poly(ethylene oxide) (PEO). 12 g of 60 wt % dispersion of a PTFE dispersion is added to the dispersion. The mixture can be placed on a roller at a for about 24 hours. Alternatively, the mixture can be hand mixed with a spatula. The mixture is placed in a spinneret with 29 ga or 30 ga needles or orifices and rotational spun at 5500-6500 rpm for three minutes. The expelled fibers are collected and sintered at 385° C. for about eight minutes.

Figure 8A:
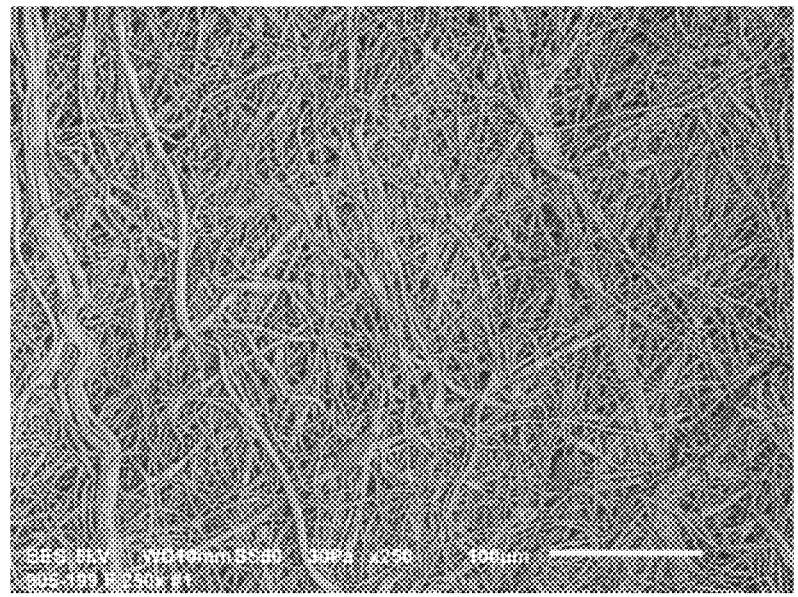
FIG. 8A is a scanning electron micrograph at 250X of a portion of another fibrous sheet.
Figure 8B:
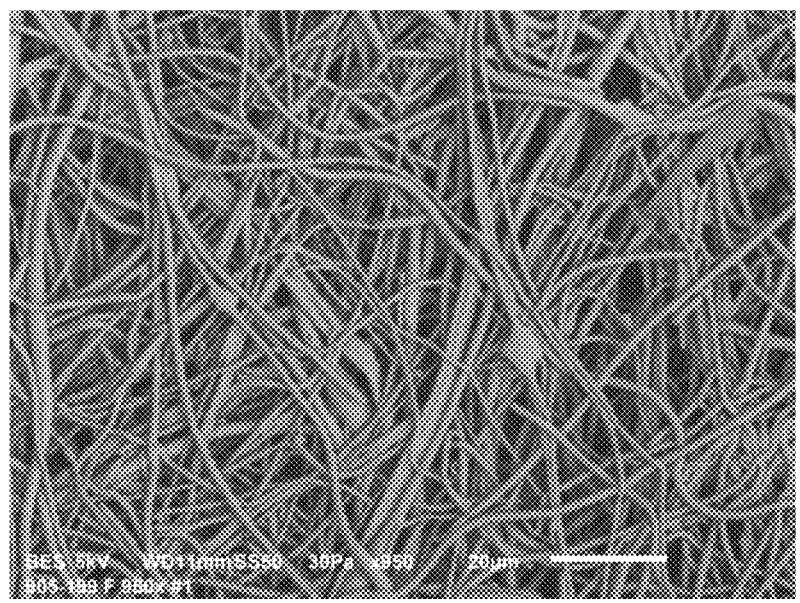
FIG. 8B is a scanning electron micrograph at 950X of a portion of the fibrous sheet of FIG. 8A.

FIG. 8A shows a SEM of a portion of the sheet formed by a rotational spinning process magnified at 250× and FIG. 8B shows the same portion magnified at 950×.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A fibrous sheet, comprising:
   a mat of fibers comprising a plurality of fibers forming a porous microstructure, wherein the plurality of fibers are formulated from a polymer matrix with a plurality of therapeutic micro or nano particles dispersed throughout the polymer matrix,
   wherein the plurality of therapeutic micro or nano particles are not eluded into a surrounding environment,
   wherein the plurality of therapeutic micro or nano particles comprise a plurality of carbon material particles,
   wherein each of the plurality of carbon material particles are larger than a diameter of each fiber of the mat of fibers, and
   wherein each of the plurality of carbon material particles are entangled by the plurality of fibers.

2. The fibrous sheet of claim 1, wherein the plurality of fibers are formed by an extrusion process.

3. The fibrous sheet of claim 2, wherein the extrusion process includes any one of rotational spinning, electrospinning, and pressure extrusion and stretching.

4. The fibrous sheet of claim 1, wherein the carbon material particles comprise any one of graphene nanosheets, graphene quantum dots, graphene nanoribbons, graphene nanoparticles, graphene oxide, pyrolytic carbon, carbon nanofibers, carbon nanotubes, fullerenes, and any combination thereof.

5. The fibrous sheet of claim 1, wherein each one of the plurality of carbon material particles has a maximum dimension of less than 0.159 mm.

6. The fibrous sheet of claim 1, wherein the therapeutic micro or nano particles comprise any one of elemental metal, metal oxide, metal colloidal, pyrolytic carbon, poly paraphenylene terephthalamide, polyamid, potassium ferrate, and calcium phosphate.

7. The fibrous sheet of claim 1, wherein the plurality of carbon material particles are exposed at a surface of fibers of the plurality of fibers.

8. The fibrous sheet of claim 1, wherein the plurality of carbon material particles completely cover a surface of fibers of the plurality of fibers.

9. A fibrous sheet, comprising:
   a mat of fibers, wherein the fibers comprise a polymer matrix and a plurality of carbon material particles that are not eluded into a surrounding environment,
   wherein each of the plurality of carbon material particles are larger than a diameter of fibers, and
   wherein each of the plurality of carbon material particles are entangled by the fibers.

10. The fibrous sheet of claim 9, wherein the fibers are formed by an extrusion process.

11. The fibrous sheet of claim 10, wherein the extrusion process includes any one of rotational spinning, electrospinning, and pressure extrusion and stretching.

12. The fibrous sheet of claim 9, wherein the polymer matrix comprises any one of polytetrafluoroethylene (PTFE), nylon 6-6, poly paraphenylene terephthalamide, polyurethane, polyethylene, polyester, and polypropylene.

13. A method of forming a fibrous sheet, comprising:
    obtaining a polymeric mixture comprising a polymer and a plurality of therapeutic micro or nano particles, wherein the plurality of therapeutic micro or nano particles comprise a plurality of carbon material particles;
    extruding the polymeric mixture to form a fibrous mat comprising a plurality of fibers; and sintering the fibrous mat,
    wherein the plurality of therapeutic micro or nano particles are configured to not elude into a surrounding environment,
    wherein each of the plurality of carbon material particles are larger than a diameter of fibers, and
    wherein each of the plurality of carbon material particles are entangled by the fibers.

14. The method of claim 13, wherein each one of the plurality of therapeutic micro or nano particles has a maximum dimension of less than 0.159 mm.

15. The method of claim 13, wherein the extruding the polymeric mixture comprises rotational spinning.

16. The method of claim 13, wherein the extruding the polymeric mixture comprises electrospinning.

17. The method of claim 13, wherein the extruding the polymeric mixture comprises pressure extruding and stretching.

18. The method of claim 13, wherein the sintering temperature is ranges from 370° C. to 390° C.

19. The method of claim 13, wherein the sintering temperature ranges from 360° C. to 400° C.

20. The method of claim 13, wherein the plurality of fibers are any one of microfibers, nanofibers, and a combination of microfibers and nanofibers.

* * * * *

UNITED STATES PATENT AND TRADEMARK OFFICE
CERTIFICATE OF CORRECTION

| | | |
|---|---|---|
| PATENT NO. | : 12,310,987 B2 | Page 1 of 1 |
| APPLICATION NO. | : 17/652552 | |
| DATED | : May 27, 2025 | |
| INVENTOR(S) | : Hall et al. | |

It is certified that error appears in the above-identified patent and that said Letters Patent is hereby corrected as shown below:

In the Claims

Column 12, Line 53, Claim 18 reads, ". . . sintering temperature is ranges..." which should read, ". . . sintering temperature ranges..."

Signed and Sealed this
Twelfth Day of August, 2025

Coke Morgan Stewart
*Acting Director of the United States Patent and Trademark Office*